United States Patent [19]

Ichihashi et al.

[11] Patent Number: 4,711,542
[45] Date of Patent: Dec. 8, 1987

[54] OPHTHALMIC DISEASE DETECTION APPARATUS

[75] Inventors: Tadashi Ichihashi, Toyohashi; Koichiro Kakizawa, Okazaki; Masunori Kawamura, Aichi, all of Japan

[73] Assignee: Kowa Company Ltd., Aichi, Japan

[21] Appl. No.: 866,582

[22] Filed: May 22, 1986

[30] Foreign Application Priority Data

May 22, 1985 [JP] Japan .................................. 60-108297

[51] Int. Cl.$^4$ ................................................ A61B 3/10
[52] U.S. Cl. .................................. 351/221; 128/303.1; 351/246
[58] Field of Search ............... 351/219, 205, 221, 246'; 128/303.1, 303.17; 356/335, 336; 204/182.8

[56] References Cited

U.S. PATENT DOCUMENTS 4,402,601  9/1983  Riva ................................. 351/221
4,582,405  4/1986  Müller et al. .................... 351/221

Primary Examiner—Rodney B. Bovernick
Assistant Examiner—Dzierzynski, P. M.
Attorney, Agent, or Firm—Bruce L. Adams; Van C. Wilks

[57] ABSTRACT

An apparatus for detecting ophthalmic diseases such as a cataract in the lens of a patient's eye which includes means for focussing a laser beam at a selected spot in the lens of an eye, and according to which the light back-scattered from the eye are photoelectrically detected and converted into an electrical signal which is subsequently used to determine an autocorrelation function relating to the fluctuation of intensity of the back-scattered light over time, and to derive therefrom a protein particle distribution essential to ophthalmic disease detection.

4 Claims, 4 Drawing Figures

OPHTHALMIC DISEASE DETECTION APPARATUS

BACKGROUND OF THE INVENTION

1. Field of the Invention

This invention relates to an apparatus for detecting ophthalmic diseases in the lens of a patient's eye, and more particularly to an apparatus for detecting ophthalmic diseases by irradiating a laser beam via an optical system at one spot in the interior of a patient's eye, and detecting the laser light back-scattered therefrom.

2. Description of the Prior Art

Cataracts are a common ophthalmic disease in which protein particles normally found in human crystalline lenses increase in size causing turbidity in the lens. Measuring the size and diameter of these protein particles is essential to effecting early detection of a cataract condition and to preparing preventative medical treatment thereof.

A human eye comprises transparent elements such as a cornea, crystalline lens, etc. Fine protein particles float amongst these transparent elements and exhibit Brownian movement. In normal disease-free eyes the protein particles are distributed in the form of small diameter particles, however in turbid eyes the particles are of a larger diameter.

There is known in the art an apparatus for measuring the diameter of protein particles in the human eye which comprises a laser for generating and then imaging a laser beam on a selected portion of the crystalline lens of the eye of a patient to be measured. Protein particles exhibiting Brownian movement pass through the portion of the lens of the eye on which the laser beam is focussed causing the back-scattering thereof. Part of the laser light back-scattered in this manner is directed toward the eyepiece of a binocular microscope for monitoring, and another part thereof is directed toward a photomultiplier which converts the intensity of the back-scattered light into an electrical signal. This signal is input to an autocorrelator which determines an autocorrelation function with respect to the fluctuation of the intensity of the back-scattered beam over time. The thus obtained correlation value is then used to calculate the relaxation time of the fluctuation of the intensity of the back-scattered beam. Accordingly, a diffusion coefficient may be further derived based thereon which may then be used to determine the diameter of the protein particles.

According to a prior art ophthalmic disease detection apparatus of this type, it is possible to measure the average diameter of the protein particles, however the measuring of the distribution of the particles in the crystalline lens remains problematic.

SUMMARY OF THE INVENTION

It is therefore an object of the present invention to provide an apparatus for detecting ophthalmic diseases which is capable of measuring the distribution of the protein particles in the eye.

It is another object of the present invention to provide an apparatus for detecting ophthalmic diseases which is capable of effecting an easy and precise detection thereof.

In accordance with the present invention, the ophthalmic disease detection apparatus disclosed herein includes means for focussing a laser beam at a selected spot in the lens of a patient's eye. The light which is back-scattered from the eye is photoelectrically detected and converted to an electrical signal which is used to determine an autocorrelation function and to calculate therefrom a protein particle distribution essential to ophthalmic disease detection. According to the invention, a distribution of the protein particles in a patient's eye is evaluated based on the output from the autocorrelator, hence it is possible not only to calculate the diameter of the particles but also to easily calculate a distribution showing what kind of particles exist in what proportion. Thus an effective means for measuring ophthalmic diseases may be realized.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Figure 1:
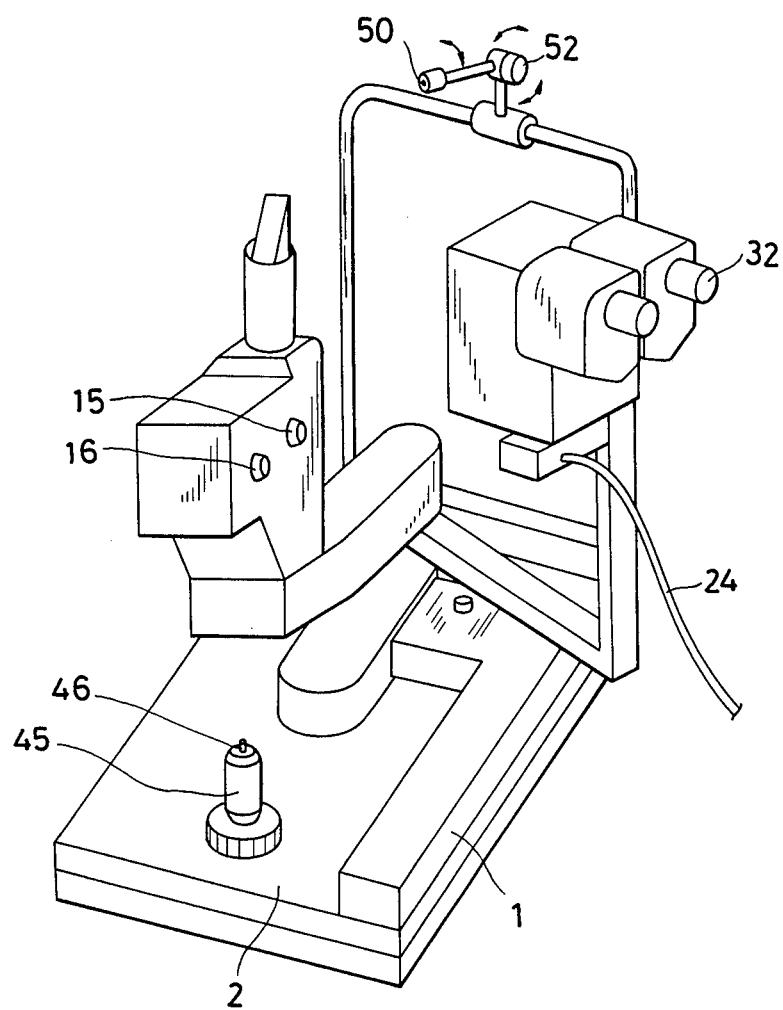
FIG. 1 is a schematic perspective view showing the whole appearance of the apparatus of the present invention.
Figure 2:
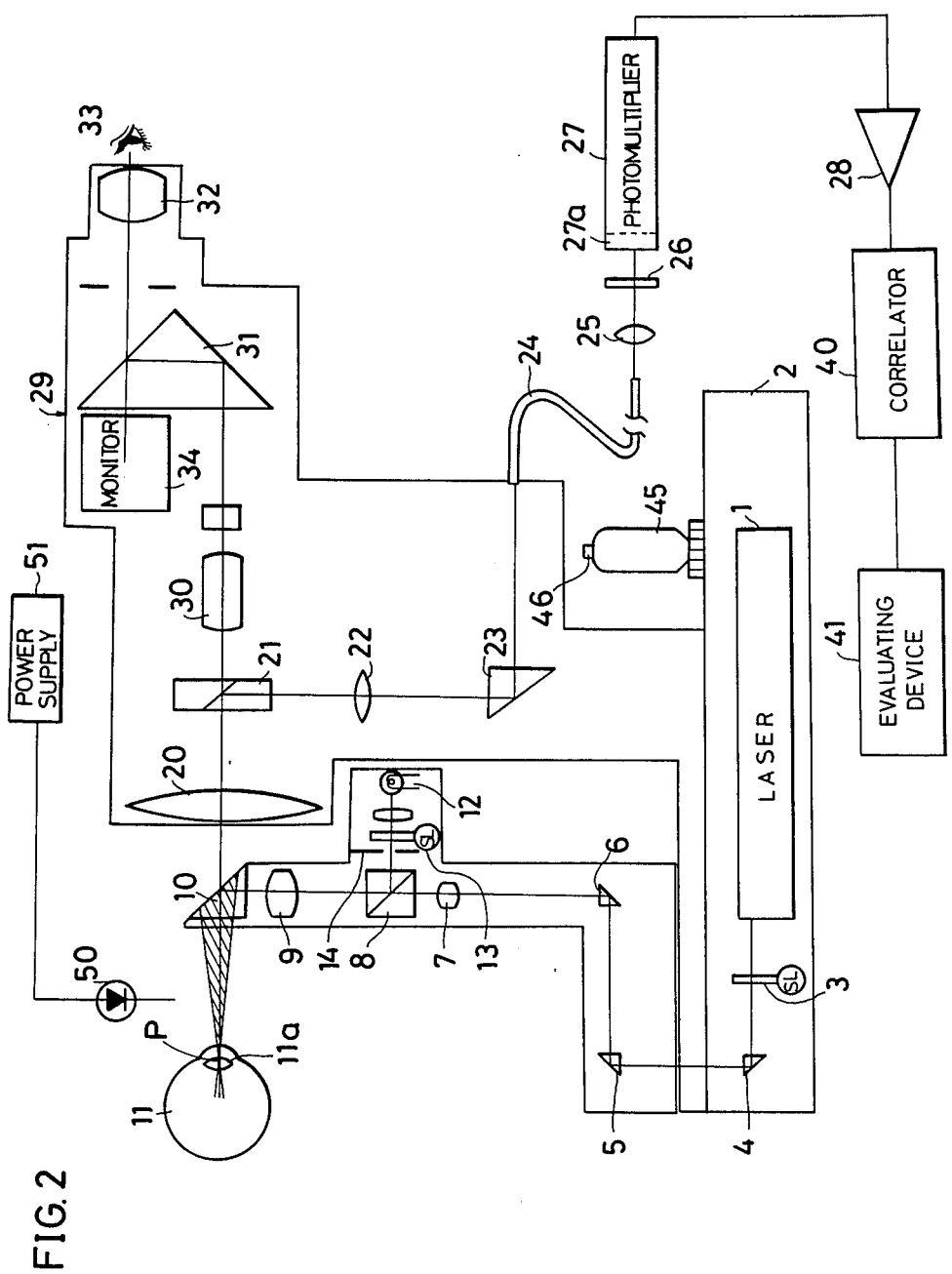
FIG. 2 is a block diagram showing the optical arrangement of the apparatus.

FIG. 1 and FIG. 2 show the general arrangement of an ophthalmic disease detection apparatus according to the present invention. In the drawings, reference numeral 1 indicates a helium-neon or argon type laser light source. The laser light source 1 is provided on a base 2. The light emitted from the laser light source 1 is passed through a laser filter 3, prisms 4, 5, and 6, a lens 7, a beam splitter 8, a lens 9, and a prism 10, and imaged so as to converge at one spot on a crystalline lens 11a of a patient's eye 11.

A slit light source 12 is provided in the laser emitting portion, and the light emitted from this light source 12 passes through a slit light shutter 13, a slit 14, and via the beam splitter 8, the lens 9 and the prism 10, whereupon it is imaged as a slit image on the crystalline lens 11a. Because the light emitted from the above mentioned laser light source 1 is imaged as a spot of light, the slit light image is intended to illuminate the periphery of the light spot and thereby make the verification of the location of the spot image easy.

Adjustment as well as switching of the length of the slit along the lengthwise dimension of the slit 14 are carried out according to an adjust knob 15 and a switch knob 16, respectively.

Part of the laser light back-scattered from the measurement spot in the crystalline lens 11a passes through the objective lens 20 of the detector 29, and is then divided by a beam splitter 21, whereupon a portion of the light passes through a lens 22, a prism 23, an optical fiber 24, a lens 25, and a shutter 26, and strikes a photomultiplier 27 which performs the function of a photoelectric converter. Another portion of the back-scattered light divided by the beam splitter 21 is directed in another direction and passes through a zoom lens 30 and a prism 31, whereupon it is enlarged and imaged on a monitoring plate 34. This image may be observed by an examiner 33 through an eyepiece 32.

The output of the photomultiplier 27 is passed through an amplifier 28 and input to a correlator 40, whereupon the correlation relating to the fluctuation of the intensity of back-scattered light detected by the photoelectric converter over time can be calculated. The output of the correlator 40 is input to an evaluating device 41 where the distribution of particle diameters is investigated.

In the present invention, an eye attention lamp 50 comprising a light emitting diode fed by a power supply 51 is disposed in such a position as to enable the patient to fix the gaze of his eye thereto. The shade of light emitted by the eye attention lamp 50 is selected so as to differ from the shade of light emitted by the laser light source 1. As an example, if the light emitted from the laser light source is red, the light emitted by the eye attention lamp may be green. This eye attention lamp 50 may be swivelled in the directions indicated by the arrows according to a linkage 52, and hence is adjustable to the optimal position for any given patient.

An input device such as, for example, a joy stick 45 equipped with a push-button 46 is provided on the base 2, the manipulating of which effectuates the insertion of the laser filter 3, the slit light shutter 13, and the shutter 26 into the optical system, as well as the extraction of same therefrom.

The operation of an apparatus with such an arrangement will be explained below. Immediately preceding measurement, the light source 12 is turned on, and the slit image of the slit 14 is passed through the beam splitter 8, the prism 10 and the lens 9 and imaged on the crystalline lens 11a over an area that covers a measurement spot P. Next, light from the laser light source 1 is passed through the optical arrangement of same and caused to converge on the measurement spot P.

Figure 3:
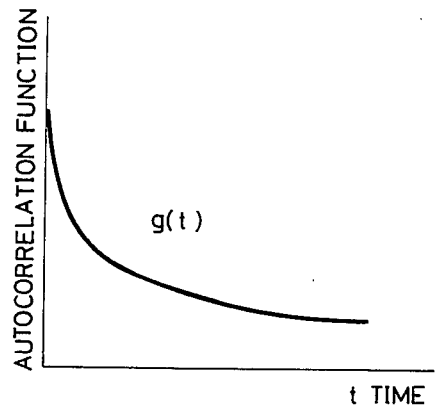
FIG. 3 is a diagram showing the output of the correlator.

The laser light beam is then back-scattered from the spot P, whereupon the beam splitter 21 directs a portion of the scattered light in the direction of the examiner 33 for observation, and simultaneously sends another portion thereof to the photomultiplier 27 via the optical system comprising the lens 22, the prism 23, and the optical fiber 24. The photomultiplier 27 detects the intensity of the back-scattered light scattered by the protein particles in the crystalline lens 11a, subsequent to which the correlator 40 determines the correlation function relating to how the intensity of the light fluctuates over time. An example output of the correlator 40 is shown in FIG. 3.

If n types of particle diameters strike laser light at the points in the crystalline lens exhibiting Brownian movement, the calculation of the autocorrelation function g(t) of the scattered light using the correlator 40 is carried out as follows:

$$g(t) = C_0 + (C_1 e^{-\Gamma t} + C_2 e^{31\Gamma 2t} + \ldots + C_n e^{-\Gamma nt})^2$$

$\Theta k(k=1, 2, \ldots, n)$ is a constant determined according to the diameter (radius) of the respective particles, and the following relational expression applies.

$$\Gamma k = \frac{KB \cdot T}{6\pi a k \eta} \left( \frac{4\pi}{\lambda} n \cdot \sin \frac{\theta}{2} \right)^2$$

where,
KB = Boltzmann's constant
T = absolute temperature
ak = particle radius
$\eta$ = viscosity coefficient
$\lambda$ = wavelength of the laser light
n = index of refraction
$\theta$ = angle of scattering.

Further, Co express the weight of the D.C. components of g(t), Ck (k=1, 2, ..., n) the weight of each exponential component, and the ratio thereof indicates the diffusion intensity ratio resulting from the respective particle diameters.

Figure 4:
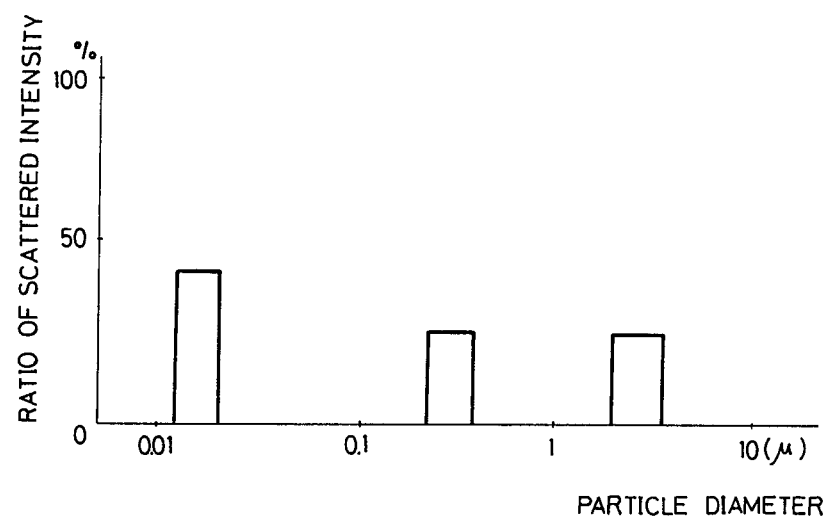
FIG. 4 is a diagram showing particle distribution.

If an analysis of g(t) values output from the correlator 40 is performed with the evaluating device 41 according to the above mentioned expressions, a distribution of the measured particles is obtained which is shown in FIG. 4. In FIG. 4, the horizontal axis represents particle diameter, and the vertical axis represents the ratio of scattered intensity resulting from the various particle diameters.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. An apparatus for detecting ophthalmic diseases in the lens of a patient's eye comprising:
   a laser for producing a laser beam;
   means for focussing said laser beam at a selected spot in the lens of said patient's eye;
   photoelectric converting means for receiving light scattered from said lens and converting same into an electric signal;
   an autocorrelator for determining an autocorrelation function in response to an electrical signal received from said photoelectric converting means; and
   means for calculating the distribution of protein particles in the lens of said eye in terms of the diameters thereof in response to an output signal from said autocorrelator.

2. An apparatus according to claim 1, wherein said autocorrelator determines the correlation function relating to the fluctuation of intensity of the scattered light over time.

3. An apparatus according to claim 2, wherein said photoelectric converting means is a photomultiplier.

4. An apparatus according to claim 1, wherein said photoelectric converting means is a photomultiplier.

* * * * *